(12) United States Patent
Flanagan et al.

(10) Patent No.: US 11,259,778 B2
(45) Date of Patent: Mar. 1, 2022

(54) ALL OPTICAL ATRIAL ABLATION DEVICE

(71) Applicant: Boston Scientific Scimed Inc., Maple Grove, MN (US)

(72) Inventors: Aiden Flanagan, Kilcogan (IE); Daniel J. Foster, St. Paul, MN (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 695 days.

(21) Appl. No.: 15/928,075

(22) Filed: Mar. 21, 2018

(65) Prior Publication Data

US 2018/0271491 A1    Sep. 27, 2018

Related U.S. Application Data

(60) Provisional application No. 62/475,167, filed on Mar. 22, 2017.

(51) Int. Cl.
*A61B 8/00* (2006.01)
*A61L 31/08* (2006.01)
(Continued)

(52) U.S. Cl.
CPC .......... *A61B 8/4477* (2013.01); *A61B 5/0095* (2013.01); *A61B 5/0097* (2013.01);
(Continued)

(58) Field of Classification Search
CPC ... A61B 8/4477; A61B 5/0095; A61B 5/0097; A61B 8/445; A61B 8/5215; A61B 8/54;
(Continued)

(56) References Cited

U.S. PATENT DOCUMENTS 5,957,941 A    9/1999 Ream
6,813,401 B1   11/2004 Mills et al.
(Continued)

FOREIGN PATENT DOCUMENTS

EP    1159036 B1    12/2001
EP    1750216 A1    2/2007
(Continued)

OTHER PUBLICATIONS

Acquafresca, A. et al. Toward Virtual Biopsy Through an All Fiber Optic Ultrasonic Miniaturized Transducer: A Proposal. IEEE Transactions On Ultrasonics, Ferroelectrics, And Frequency Control, 50(10):1325-1335, Oct. 2003.
(Continued)

*Primary Examiner* — Amelie R Davis
*Assistant Examiner* — Helene Bor
(74) *Attorney, Agent, or Firm* — Faegre Drinker Biddle & Reath LLP

(57) ABSTRACT

A catheter system includes a catheter. The catheter includes a catheter tip and an ultrasound assembly at least partially positioned within the catheter tip. The ultrasound assembly includes a first optical fiber coupled to an optical-to-ultrasound transducer and a second optical fiber coupled to an ultrasound-to-optical transducer. The optical-to-ultrasound transducer is configured to generate an ultrasound signal in response to a pulsed optical signal. The ultrasound-to-optical transducer is configured to generate an optical signal in response to a received ultrasound signal.

15 Claims, 7 Drawing Sheets

(51) Int. Cl.
| | |
|---|---|
| *A61B 5/00* | (2006.01) |
| *A61B 8/08* | (2006.01) |
| *A61B 18/00* | (2006.01) |
| *A61B 18/14* | (2006.01) |
| *A61B 90/00* | (2016.01) |
| *A61B 8/12* | (2006.01) |
| *A61B 5/0215* | (2006.01) |

(52) U.S. Cl.
CPC ............ *A61B 8/445* (2013.01); *A61B 8/5215* (2013.01); *A61B 8/54* (2013.01); *A61B 18/00* (2013.01); *A61B 18/1492* (2013.01); *A61L 31/08* (2013.01); *A61B 5/0066* (2013.01); *A61B 5/0084* (2013.01); *A61B 5/0215* (2013.01); *A61B 8/12* (2013.01); *A61B 8/4483* (2013.01); *A61B 2018/00023* (2013.01); *A61B 2018/00577* (2013.01); *A61B 2018/00642* (2013.01); *A61B 2018/00738* (2013.01); *A61B 2018/00791* (2013.01); *A61B 2090/3614* (2016.02); *A61B 2090/3784* (2016.02); *A61B 2562/0247* (2013.01)

(58) Field of Classification Search
CPC ................ A61B 18/00; A61B 18/1492; A61B 2090/3614; A61B 2090/3784; A61B 5/0066; A61B 5/0084; A61B 5/0215; A61B 8/12; A61B 8/4483; A61B 2018/00023; A61B 2018/00577; A61B 2018/00642; A61B 2018/00738; A61B 2018/00791; A61B 2562/0247; A61L 31/08

See application file for complete search history.

(56) References Cited

U.S. PATENT DOCUMENTS

| | | | |
|---|---|---|---|
| 7,399,300 | B2 | 7/2008 | Bertolero et al. |
| 8,197,721 | B2 | 6/2012 | Stuart et al. |
| 2004/0131299 | A1* | 7/2004 | Adoram ............... A61B 5/0095 385/12 |
| 2006/0100489 | A1* | 5/2006 | Pesach ............... G01N 29/2418 600/310 |
| 2006/0241572 | A1* | 10/2006 | Zhou ..................... A61B 8/4483 606/7 |
| 2008/0108867 | A1 | 5/2008 | Zhou |
| 2008/0154257 | A1 | 6/2008 | Sharareh et al. |
| 2009/0177095 | A1 | 7/2009 | Aeby et al. |
| 2010/0041986 | A1* | 2/2010 | Nguyen ............... A61B 5/6852 600/427 |
| 2010/0069797 | A1 | 3/2010 | Cain et al. |
| 2010/0087732 | A1* | 4/2010 | Eberle ................ A61B 1/00082 600/437 |
| 2012/0136351 | A1 | 5/2012 | Weekamp et al. |
| 2013/0204134 | A1* | 8/2013 | Harks .................. A61B 5/4836 600/439 |
| 2014/0058244 | A1* | 2/2014 | Krocak ............... A61B 5/0095 600/407 |
| 2014/0112107 | A1 | 4/2014 | Guo et al. |
| 2014/0180056 | A1* | 6/2014 | Hoseit ..................... A61B 8/12 600/407 |
| 2014/0180119 | A1 | 6/2014 | Millett |
| 2014/0180273 | A1 | 6/2014 | Nair |
| 2014/0309632 | A1 | 10/2014 | Ogata et al. |
| 2016/0030108 | A1 | 2/2016 | Lupotti |
| 2016/0038119 | A1 | 2/2016 | Desjardins |
| 2016/0166231 | A1 | 6/2016 | Deladi |
| 2017/0079529 | A1* | 3/2017 | Mak ..................... A61B 5/0066 |

FOREIGN PATENT DOCUMENTS

| | | |
|---|---|---|
| EP | 1935332 A2 | 6/2008 |
| WO | WO2014174305 A2 | 10/2014 |
| WO | 2016113543 A1 | 7/2016 |

OTHER PUBLICATIONS

Baac, H. W. et al. Carbon nanotube composite optoacoustic transmitters for strong and high frequency ultrasound generation. Applied Physics Letters, 97:234104-1-234104-3, 2010.

Colchester, R. J. et al. Laser-generated ultrasound with optical fibres using functionalised carbon nanotube composite coatings. Applied Physics Letters 104:173502-1-173502-4, 2014.

Fu, X. et al. Fiber-optic catheter-based polarization-sensitive OCT for radio-frequency ablation monitoring. Opt. Lett., 39(17):5066-5069, Sep. 1, 2014.

Hou, Y. et al. Optical Generation of High Frequency Ultrasound Using Two-Dimensional Gold Nanostructure. Applied Physics Letters, 89:093901-1-093901-3, 2006.

International Search Report and Written Opinion issued in PCT/US2018/023670, dated Jul. 9, 2018, 12 pages.

Luna Innovations Incorporated. Fiberoptic Shape Sensing: Current State of Technology. Document#: SS00021-D-TS, Revision 003, pp. 1-6 Jun. 21, 2013.

Mosse, C. A. et al. Fiber-optic Ultrasound Transducers With Carbon/PDMS Composite Coatings, Photons Plus Ultrasound: Imaging and Sensing 2014, edited by Oraevsky, A. A. and Lihong V. Wang, Proc. of SPIE, 8943:89430P-1-89430P-7.

Noimark, S. et al. Carbon-Nanotube-PDMS Composite Coatings on Optical Fibers for All-Optical Ultrasound Imaging. Advanced Functional Materials, Materials Views, 2016:8390-8396.

Noimark, S. et al. Supporting Information for Adv. Funct. Mater., DOI: 10.1002/adfm.201601337, Carbon-Nanotube-PDMS Composite Coatings on Optical Fibers for All-Optical Ultrasound Imaging.

Pinet, E. Pressure Measurement With Fiber-Optic Sensors: Commercial Technologies and Applications. 21st International Conference on Optical Fiber Sensors, edited by Bock, W. J. et al., Proc. of SPIE, 7753-775304-1-775304-4, 2011.

Tsui, P. et al. Monitoring Radiofrequency Ablation Using Ultrasound Envelope Statistics and Shear Wave Elastography in the Periablation Period: An In Vitro Feasibility Study. PLoS ONE, 11(9):1-14, Sep. 7, 2016.

Xia, W. et al. In-plane ultrasonic needle tracking using a fiber-optic hydrophone. Medical Physics, 42:5983-5991, 2015.

Zhou, Z. et al. A survey of ultrasound elastography approaches to percutaneous ablation monitoring. Proc. Institution of Mechanical Engineers Part H, Journal of Engineering in Medicine, Review Article, 228(10):1069-1082, 2014.

* cited by examiner

ALL OPTICAL ATRIAL ABLATION DEVICE

CROSS-REFERENCE TO RELATED APPLICATION

This application claims priority to Provisional Application No. 62/475,167, filed Mar. 22, 2017, which is herein incorporated by reference in its entirety.

TECHNICAL FIELD

The present disclosure relates generally to medical devices and, more particularly, to systems, devices and methods related to catheters used to perform ablation functions.

BACKGROUND

Cardiac ablation is a procedure by which cardiac tissue is treated to inactivate the tissue. The tissue targeted for ablation may be associated with improper electrical activity, for example. Cardiac ablation can lesion the tissue and prevent the tissue from improperly generating or conducting electrical signals.

SUMMARY

In Example 1, a catheter system includes a catheter. The catheter includes a catheter tip and an ultrasound assembly at least partially positioned within the catheter tip. The ultrasound assembly includes a first optical fiber coupled to an optical-to-ultrasound transducer and a second optical fiber coupled to an ultrasound-to-optical transducer. The optical-to-ultrasound transducer is configured to generate an ultrasound signal in response to a pulsed optical signal. The ultrasound-to-optical transducer is configured to generate an optical signal in response to a received ultrasound signal.

In Example 2, the catheter system of Example 1, wherein the optical-to-ultrasound transducer is a coating applied to a distal end of the first optical fiber.

In Example 3, the catheter system of Example 2, wherein the coating comprises at least one of an elastomer, carbon nanotubes, gold nanostructures, polymer, carbon black, graphene, and graphite.

In Example 4, the catheter system of any of Examples 1-3, further comprising third, fourth, and fifth optical fibers, each coupled to its own ultrasound-to-optical transducer, each ultrasound-to-optical transducer configured to generate an optical signal in response to a received ultrasound signal.

In Example 5, the catheter system of any of Examples 1-4, wherein the first optical fiber has a greater diameter than the other optical fibers.

In Example 6, the catheter system of any of Examples 1-5, wherein the first optical fiber is positioned centrally among the other optical fibers.

In Example 7, the catheter system of any of Examples 1-6, wherein the ultrasound assembly includes at least one optical fiber configured for one of force sensing, pressure sensing, and shape sensing.

In Example 8, the catheter system of any of Examples 1-7, further comprising at least one optical coherence tomography (OCT) emitting/receiving optical fiber configured to emit light and receive light reflected back to the OCT emitting/receiving optical fiber.

In Example 9, the catheter system of any of Examples 1-8, further comprising a laser source coupled to the first optical fiber, wherein the laser source is configured to generate the pulsed optical signal.

In Example 10, the catheter system of any of Examples 1-9, wherein the optical signal corresponds to a signature of a tissue structure.

In Example 11, the catheter system of Example 10, wherein the signature comprises a plurality of pixels, each of which is indicative of tissue structure at different depths of the tissue.

In Example 12, the catheter system of any of Examples 10-11, further comprising a control system comprising a memory and a processor, wherein the control system is configured to receive the optical signal, compare the signature to a previously-received signature, and based on the comparison, determine that the tissue has been ablated.

In Example 13, the catheter system of any of Examples 10-11, further comprising a control system comprising a memory and a processor, wherein the control system is configured to receive the optical signal, compare a signature of a first portion of tissue to a signature of a second portion of tissue, and based on the comparison, determine that the first portion of tissue has been ablated.

In Example 14, the catheter system of any of the Examples 12-13, wherein the comparison includes comparing pixel brightness.

In Example 15, the catheter system of any of the Examples 12-13, wherein the comparison includes comparing pixel contrast.

In Example 16, a catheter system includes a catheter. The catheter includes a catheter tip and an ultrasound assembly at least partially positioned within the catheter tip. The ultrasound assembly includes a first optical fiber coupled to an optical-to-ultrasound transducer and a second optical fiber coupled to an ultrasound-to-optical transducer. The optical-to-ultrasound transducer is configured to generate an ultrasound signal in response to a pulsed optical signal. The ultrasound-to-optical transducer is configured to generate an optical signal in response to a received ultrasound signal.

In Example 17, the catheter system of Examples 16, wherein the optical-to-ultrasound transducer is a coating applied to a distal end of the first optical fiber.

In Example 18, the catheter system of Example 17, wherein the coating comprises at least one of an elastomer, carbon nanotubes, gold nanostructures, polymer, carbon black, graphene, and graphite.

In Example 19, the catheter system of Example 16, wherein the ultrasound assembly further comprises third, fourth, and fifth optical fibers, each coupled to its own ultrasound-to-optical transducer, each ultrasound-to-optical transducer configured to generate an optical signal in response to a received ultrasound signal.

In Example 20, the catheter system of Example 19, wherein the first optical fiber is positioned centrally among the other optical fibers.

In Example 21, the catheter system of Example 16, wherein the first optical fiber has a greater diameter than the other optical fibers.

In Example 22, the catheter system of Example 16, wherein the catheter tip includes a cooling chamber, and wherein a distal end of the first optical fiber is coupled to a proximal end of the cooling chamber.

In Example 23, the catheter system of any of Examples 1-22, further comprising a temperature sensor positioned within the catheter tip adjacent the distal end of the first optical fiber.

In Example 24, the catheter system of Example 16, wherein the optical signal corresponds to a signature of a tissue structure.

In Example 25, the catheter system of Example 24, further comprising a control system comprising a memory and a processor, wherein the memory stores instructions that cause the processor to receive the optical signal, compare the signature to a previously-received signature, and based on the comparison, determine that the tissue has been ablated.

In Example 26, the catheter system of Example 25, wherein the signature comprises a plurality of pixels, each of which is indicative of tissue structure at different depths of the tissue, and wherein the comparison includes comparing one of pixel brightness and pixel contrast.

In Example 27, the catheter system of Example 24, further comprising a control system comprising a memory and a processor, wherein the memory stores instructions that cause the processor to receive the optical signal, compare a signature of a first portion of tissue to a signature of a second portion of tissue, and based on the comparison, determine that the first portion of tissue has been ablated.

In Example 28, the catheter system of Example 27, wherein the signature comprises a plurality of pixels, each of which is indicative of tissue structure at different depths of the tissue, and wherein the comparison includes comparing one of pixel brightness and pixel contrast.

In Example 29, the catheter system of Example 16, wherein the first optical fiber includes a first set of optical gratings, wherein the optical-to-ultrasound transducer is configured to generate an ultrasound signal at a first frequency. The catheter further comprises a third optical fiber coupled to a second optical-to-ultrasound transducer and having a second set of optical gratings. The second optical-to-ultrasound transducer is configured to generate an ultrasound signal at a second frequency. The catheter further comprises a fourth optical fiber coupled to a third optical-to-ultrasound transducer and having a third set of optical gratings. The third optical-to-ultrasound transducer is configured to generate an ultrasound signal at a third frequency.

In Example 30, the catheter system of Example 29, further comprising a first optical coupler configured to split light between an intermediate optical fiber and the first optical fiber; and a second optical coupler configured to split light from the intermediate optical fiber to the third and fourth optical fibers.

In Example 31, a method for monitoring tissue ablation using an ultrasound assembly including a first optical fiber and a second optical fiber. The method includes transmitting a pulsed optical signal through the first optical fiber to an optical-to-ultrasound transducer, converting the pulsed optical signal into an ultrasound signal, and converting a reflected ultrasound signal into an output optical signal via an ultrasound-to-optical transducer. The output optical signal is indicative of a current tissue structure. The method further includes comparing the current tissue structure to a previous tissue structure and, based on the comparison, determining that a portion of tissue has been damaged by ablation.

In Example 32, the method of Example 31, wherein the output optical signal is transmitted via the second optical fiber.

In Example 33, the method of Example 31, wherein the output optical signal corresponds to a signature indicative of the current tissue structure, and wherein the comparison includes comparing a current signature with a previous signature.

In Example 34, the method of Example 33, wherein the signature includes a plurality of pixels.

In Example 35, the method of Example 33, wherein the comparison includes comparing a characteristic of the plurality of pixels to determine that a portion of tissue has been damaged by ablation.

In Example 36, the method of Example 35, wherein the characteristic includes at least one of pixel brightness and pixel contrast.

In Example 37, the method of Example 34, wherein each of the plurality of pixels is indicative of tissue structure at a different depth of the tissue.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
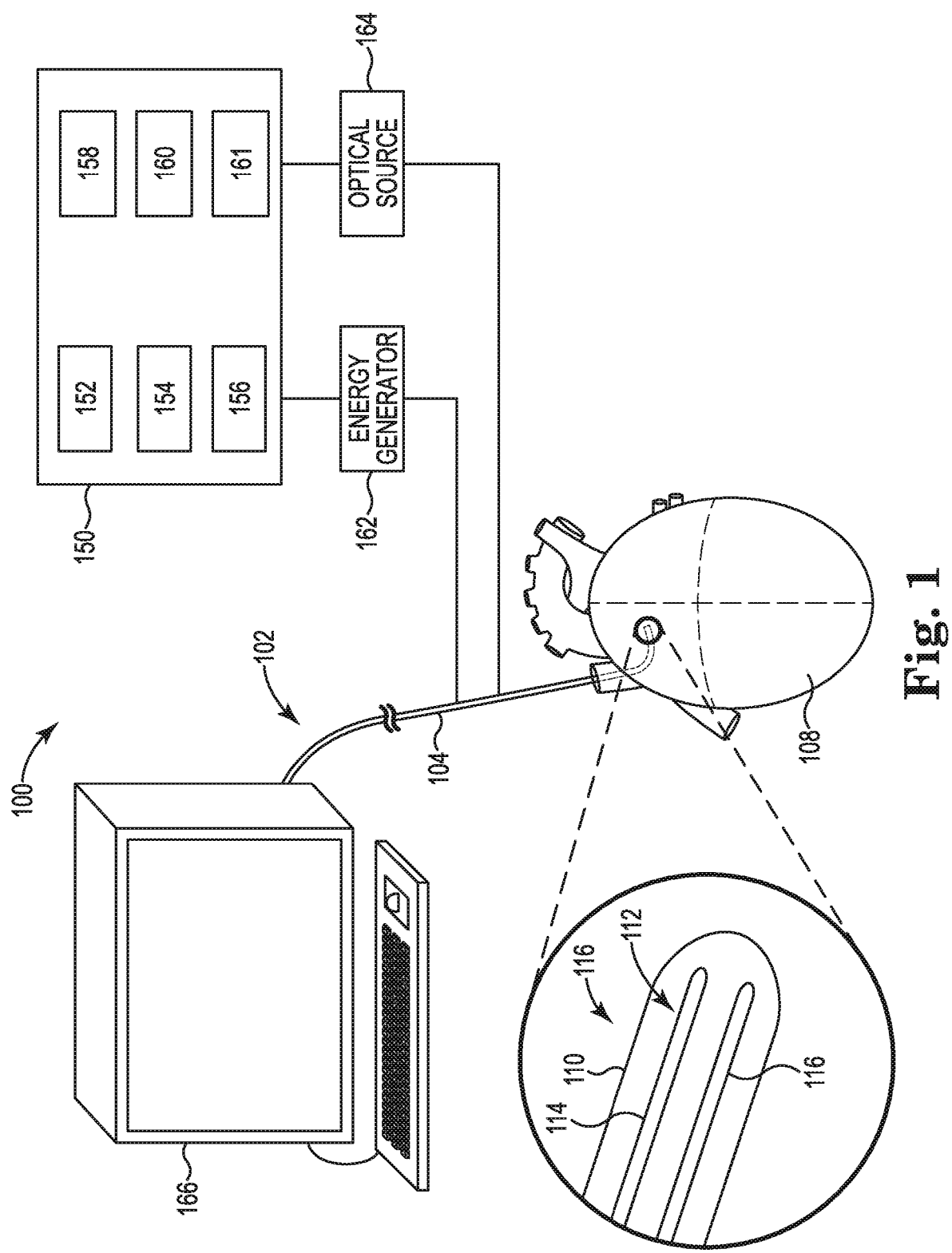
FIG. 1 shows a catheter system, in accordance with certain embodiments of the present disclosure.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Various cardiac abnormalities can be attributed to improper electrical activity of cardiac tissue. Such improper electrical activity can include, but is not limited to, generation of electrical signals, conduction of electrical signals, and/or compression of the tissue in a manner that does not support efficient and/or effective cardiac function. For example, an area of cardiac tissue may become electrically active prematurely or otherwise out of synchrony during the cardiac cycle, causing the cardiac cells of the area and/or adjacent areas to contract out of rhythm. The result is an abnormal cardiac contraction that is not timed for optimal cardiac output. In some cases, an area of cardiac tissue may provide a faulty electrical pathway (e.g., a short circuit) that causes an arrhythmia, such as atrial fibrillation or supraventricular tachycardia. In some cases, inactive tissue (e.g., scar tissue) may be preferable to malfunctioning cardiac tissue.

Cardiac ablation is a procedure by which cardiac tissue is treated to inactivate the tissue. The tissue targeted for ablation may be associated with improper electrical activity, as described above. Cardiac ablation can lesion the tissue and prevent the tissue from improperly generating or conducting electrical signals. For example, a line, a circle, or other formation of ablated cardiac tissue can block the propagation of errant electrical signals. In some cases, cardiac ablation is intended to cause the death of cardiac tissue and to have scar tissue reform over the lesion, where the scar tissue is not associated with the improper electrical activity. Ablation therapies include radiofrequency (RF) ablation, cyroablation, microwave ablation, laser ablation, electroporation ablation, and surgical ablation, among others.

During an ablation procedure, an ablation tool such as a catheter with one or more ablation electrodes is advanced into contact with a target area of tissue where ablation energy (e.g., RF energy) is to be directed into the target tissue to ablate the tissue. Attempts to assess aspects of tissue ablation can involve measuring and monitoring parameters such as temperature, impedance, and/or force near the ablation site. But, these parameters do not directly monitor lesion formation. Features of the present disclosure are accordingly directed to systems, methods, and devices that assist with monitoring tissue ablation.

FIG. 1 shows a system 100 including a catheter 102 comprising an elongated catheter body 104 and a catheter tip 106, which is configured to be positioned within a heart 108. The catheter 102 includes an ablation electrode 110 coupled to the catheter tip 106. In operation, the ablation electrode 110 contacts targeted cardiac tissue to deliver ablative energy to the cardiac tissue, thus ablating the tissue to form a lesion, which can treat cardiac rhythm disturbances or abnormalities. The ablation electrode 110 in FIG. 1 is shown as radio frequency (RF) ablation electrode, which delivers RF energy to the cardiac tissue. Although the present disclosure primarily discusses RF-ablation approaches, features of the present disclosure are applicable to other types of ablation approaches such as cyroablation, microwave ablation, etc.

The catheter tip 106 includes an optics-based ultrasound assembly 112. The optics-based ultrasound assembly 112 is distinct from approaches that utilize piezo transducers to generate ultrasound signal. Piezo-based ultrasound approaches require, among other things, electrical wires and a larger volume of space compared to the optics-based ultrasound assembly 112. The ultrasound assembly 112, along with various components of a control system 150, is configured to assess, monitor, and control various aspects of an ablation procedure in real-time. The ultrasound assembly 112 emits an ultrasonic signal towards tissue and receives a responsive ultrasonic signal indicative of various tissue ablation parameters.

In some embodiments, the ultrasound assembly 112 includes at least one emitting optical fiber 114 that directs a pulsed optical signal to an optical-to-ultrasound transducing element (discussed in more detail below) that is coupled to the emitting optical fiber 114. The optical-to-ultrasound transducing element is configured to generate and emit an ultrasound signal that is directed towards tissue undergoing ablation. At least a portion of the ultrasound signal can be reflected back towards the ultrasound assembly 112. The ultrasound assembly 112 also includes at least one ultrasound-to-optical transducing element (discussed in more detail below) that is coupled to a receiving optical fiber 116 and that is configured to convert the reflected ultrasound signal to an optical signal, which includes information indicative of various tissue ablation parameters. The converted optical signal is communicated, via the receiving optical fiber 116, to the control system 150.

The control system 150, discussed in more detail below, includes at least one memory 152, at least one processor 154, a measurement sub-unit 156, a mapping sub-unit 158, a display controller 160, and a navigation sub-unit 161. The system 100 also includes an energy source 162, which provides energy to the ablation electrode 110; an optical source 164, which is coupled to and provides optical energy to the emitting optical fiber 114; and a display 166—all of which can be communicatively coupled to and controlled by the control system 150. In some embodiments, the optical source 164 is a laser diode or semiconductor-based laser.

Figure 2:
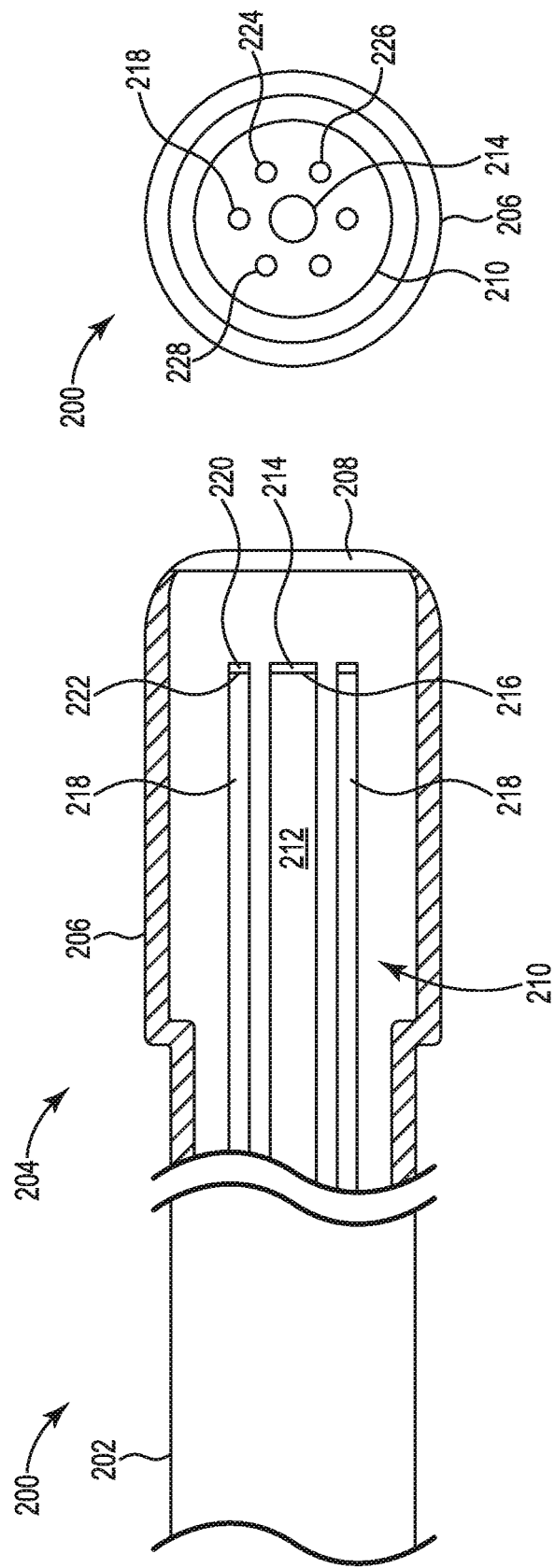
FIG. 2A shows a schematic side view of a portion of a catheter, in accordance with certain embodiments of the present disclosure.
FIG. 2B shows an end view of the catheter of FIG. 2A.
Figure 3:
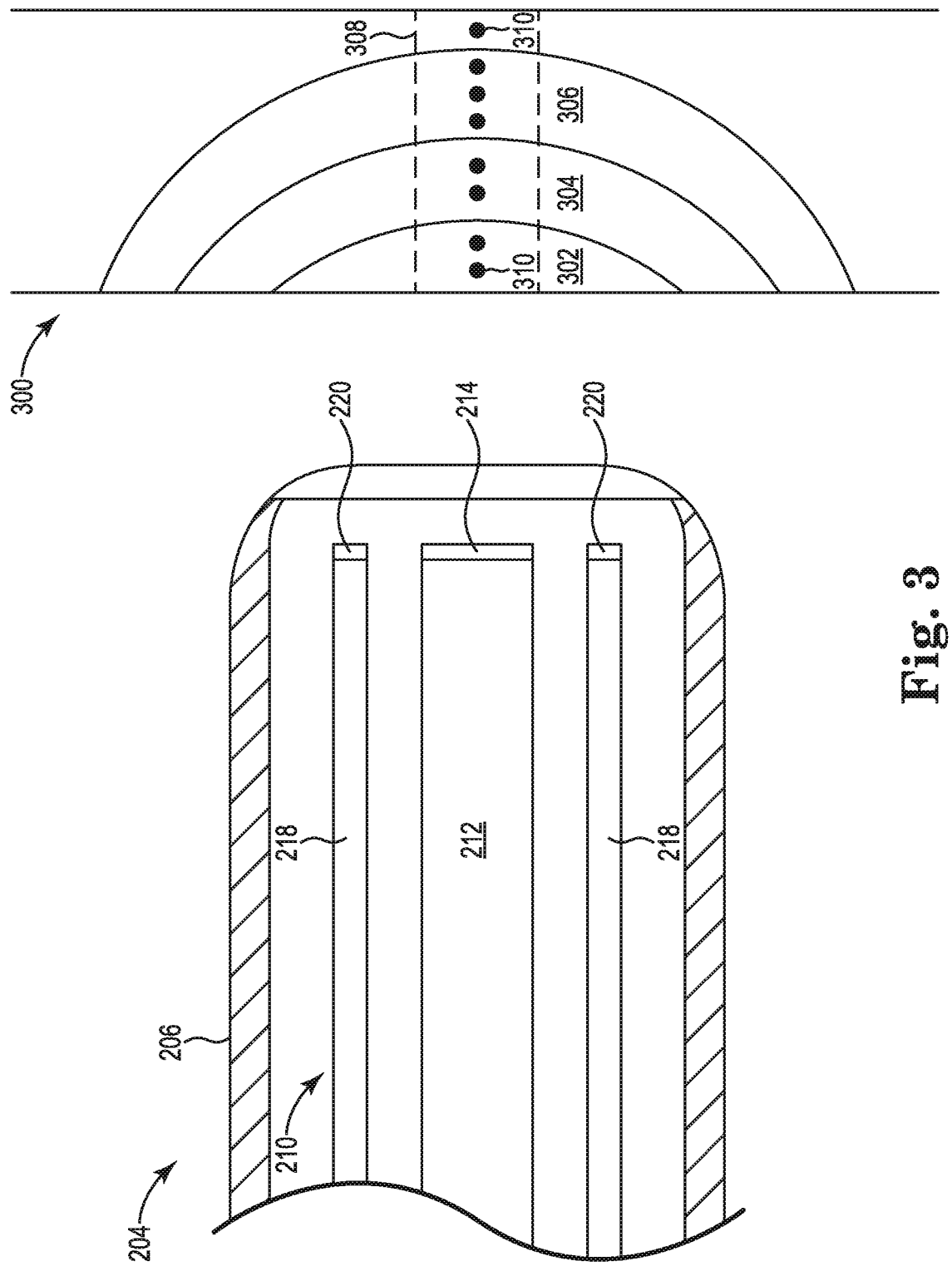
FIG. 3 shows a schematic view of the catheter of FIGS. 2A and 2B next to a target tissue ablation site.

FIGS. 2A-B provide additional detail of a catheter 200, like catheter 102 of FIG. 1, that can be used in the system 100. FIG. 2A shows a cross-section view of the catheter 200, and FIG. 2B shows a side view of a distal end of the catheter. FIG. 3 shows the catheter 200 positioned near a target tissue ablation site 300.

The catheter 200 includes an elongated catheter body 202 and a catheter tip 204. The catheter 200 also includes an ablation electrode 206 coupled to the catheter tip 204. The catheter 200 is shown as including a window 208 positioned centrally at the catheter tip 204. In some embodiments, the catheter 200 includes a plurality of windows—some of which are positioned radially around the catheter tip 204.

The catheter 200 also includes an ultrasound assembly 210 positioned within the catheter tip 204 at or near the window 208. The ultrasound assembly 210 consumes less volume within the catheter tip 204 compared to piezo-based ultrasound transducers. In some embodiments, the total diameter of the ultrasound assembly 210 at the catheter tip 204 can be 500 µm or less. It should be noted that the ultrasound assembly 210 and catheter tip 204 are not drawn to scale and that the catheter tip 204 can include features other than the ultrasound assembly 210, such as temperature sensors, navigation sensors, and fluid conduits, among other things. The ultrasound assembly 210, together with its various components, is configured to emit an ultrasonic signal and receive a responsive ultrasonic signal indicative of various tissue ablation parameters.

The ultrasound assembly 210 includes a plurality of optical fibers, including an emitting optical fiber 212. The emitting optical fiber 212 includes an optical-to-ultrasound transducing element 214 that is coupled to the emitting optical fiber 212 at the distal end 216 of the emitting optical fiber 212. The emitting optical fiber 212 is also coupled to the optical source 164. The emitting optical fiber 212 is configured to direct a pulsed or amplitude-modulated optical signal to the optical-to-ultrasound transducing element 214, which is configured to generate and emit an ultrasound signal (e.g., ultrasound waves) that is directed (e.g., propagated) towards tissue undergoing ablation. The optical signal can be pulsed at ultrasonic frequencies. In some embodiments, the optical-to-ultrasound transducing element 214 is a coating at the distal end 216 that is configured to rapidly expand and contract to generate an ultrasound signal. The coating expands and contracts in response to a quickly-pulsing optical signal that is communicated to the coating via the emitting optical fiber 212. The pulsed optical signal rapidly heats and cools the coating such that the coating rapidly expands and contracts.

The coating can comprise elastomers (e.g., polydimethylsiloxane), carbon nanotubes, gold nanostructures, polymers, graphene, carbon black, graphite, and various combinations of such materials. In some implementations, the coating is applied to the distal end 216 of the emitting optical fiber 212, and in other embodiments, an intervening material is positioned between the coating and the distal end 216 of the emitting optical fiber 212.

The ultrasound assembly 210 also includes a receiving optical fiber 218 coupled to ultrasound-to-optical transducing element 220. The ultrasound-to-optical transducing element 220 is configured to convert an ultrasound signal (including its magnitude, phase, and time-variation) reflected from tissue to a corresponding optical signal. For example, the ultrasound-to-optical transducing element 220 is configured to change its optical properties upon being excited by an ultrasound signal (e.g., ultrasound waves). In some embodiments, the ultrasound-to-optical transducing element 220 is an interferometer (e.g., a Fabry-Perot cavity) that is mounted at a distal end 222 of the receiving optical fiber 218. In other embodiments, the ultrasound-to-optical transducing element 220 is a micro-ring optical resonator. The resulting optical signal is communicated via the receiving optical fiber 218 to the control system 150 for analysis, processing, etc.

FIG. 2B shows the ultrasound assembly 210 including a single emitting optical fiber 212 and a plurality of receiving optical fibers 218. The optical fibers extend along the catheter 200 such that the emitting optical fiber 212 is coupled to the laser source 164 and the plurality of receiving optical fibers 218 are coupled to the measurement sub-unit 156 of the control system 150. The ultrasound assembly 210 can feature additional emitting fibers (each with an optical-to-ultrasound transducing element 214) and/or fewer or more receiving optical fibers (each with an ultrasound-to-optical transducing element 220). The single emitting optical fiber 212 is shown positioned centrally and surrounded by the plurality of receiving optical fibers 218. The emitting optical fiber 212 has a larger diameter than the receiving optical fibers 218 because the emitting optical fiber 212 is configured to communicate a greater amount of optical energy to cause the optical-to-ultrasound transducing element 214 to rapidly heat and cool. The receiving optical fibers 218 can be single-mode optical fibers, which can have diameters that are less than a fifth of the diameter of the emitting optical fiber 212.

FIG. 2A shows the distal ends 216, 222 of the emitting and receiving optical fibers 212, 218 positioned adjacent to and/or directly contacting the window 208. As previously mentioned, upon receiving a pulsed optical signal from the emitting optical fiber 212, the optical-to-ultrasound transducing element 214 is configured to generate and emit an ultrasound signal that is directed towards tissue undergoing ablation. The ultrasound signal impinges upon the tissue and is, at least partially, reflected back towards the ultrasound assembly 210. Each of the ultrasound-to-optical transducing elements 220, for example, converts the reflected ultrasound signal to an optical signal that is communicated via the receiving optical fibers 218 to the control system 150. In addition to space savings mentioned above, the ultrasound assembly 210 provides wider-bandwidth ultrasound signals compared to piezo-based ultrasound signals such that the reflected, converted optical signal can be used to generate high-resolution images of up-close structures. The control system 150, together with its various components, is configured to receive the converted optical signal and use the converted optical signal to assess, monitor, and control various aspects of an ablation procedure in real-time.

In some embodiments, the ultrasound assembly 210 includes one or more optical fibers, 224 and 226, configured for optical coherence tomography (OCT) imaging. The OCT optical fibers, 224 and 226, can work in conjunction and in parallel with the emitting and receiving optical fibers, 212 and 218, and control system 150 to assess, monitor, and control various aspects of an ablation procedure in real-time. OCT-based imaging can be used to generate high-resolution images of tissue and to detect changes in tissue birefringence to determine tissue properties. Although OCT-based imaging can result in high-resolution images, OCT-based imaging can be limited by the ability of emitted light to penetrate along a full depth of tissue. As such, the OCT optical fibers can work in conjunction with the emitting and receiving fibers.

The OCT optical fibers can include one or more OCT emitting/receiving optical fibers 224 and 226. Each OCT emitting/receiving optical fiber is configured to emit towards tissue and receive light reflected back to the OCT optical fiber. Each OCT emitting/receiving optical fiber can receive light that was emitted from another OCT emitting/receiving optical fiber and reflected back. The received light can be used to detect changes in birefringence of tissue fibers, which changes when ablated. The changes in birefringence can be used—along with changes monitored in the reflected ultrasound signal—to assess, monitor, and control various aspects of an ablation procedure in real-time. Although the OCT optical fibers are shown as being part of the ultrasound assembly 210, the OCT optical fibers can be part of a separate assembly and positioned and aligned in different directions than the ultrasound assembly 210.

In some embodiments, one or more of the receiving optical fibers 218 can be used for navigation purposes such as determining the position of the catheter 200 within a patient. For example, while the catheter 200 is being navigated within a patient, the receiving optical fibers 218 can be configured to send and/or receive ultrasound signals to and/or from one or more transducers positioned outside the patient, such as transducers coupled to a hand-held wand. The ultrasound signals (whether generated by the receiving optical fibers 218 or the one or more transducers) can be triangulated, for example, to determine the location of the catheter 200 within the patient. This ultrasound-based navigation approach can reduce the amount of or eliminate use of fluoroscopy dyes within a patient and reduce or eliminate a patient's exposure to radiation.

In addition to receiving optical fibers 218, the ultrasound assembly 210 can include one or more optical fibers 228 (shown in FIG. 2B) for pressure sensing, force sensing, and/or shape sensing.

For example, one or more optical fibers 228 can be configured to sense pressure and/or force via fiber-Bragg grating-based pressure sensing and/or Fabry-Perot-based pressure sensing. Fiber-Bragg-grating-based pressure sensing involves detecting changes to wavelengths resulting from strain caused by changes in pressure. Fabry-Perot-based pressure sensing involves detecting changes in an optical path length caused by either a change in the refractive index or a change in physical length of the cavity. These pressure-sensing approaches can be used to detect pressure of a heart chamber, among other things. In another example, one or more optical fibers 228 can be configured to sense shape of a heart chamber in three dimensions, for example, via measurement of strain. In particular, the axial twist and curvature along a certain length of one or more optical fibers 228 can be detected and processed to generate a three-dimensional grid of sensed tissue, for example.

As discussed above, the catheter's ultrasound assembly 210 includes a plurality of optical fibers, which can be used for a variety of purposes, such as assessing, monitoring, and/or controlling various aspects of an ablation procedure; navigation; pressure sensing; force sensing; and/or shape sensing. This reduces and/or eliminates use of other types of non-optical sensors and related circuitry and permits use of multiple sensing approaches in a compact catheter.

Figure 4:
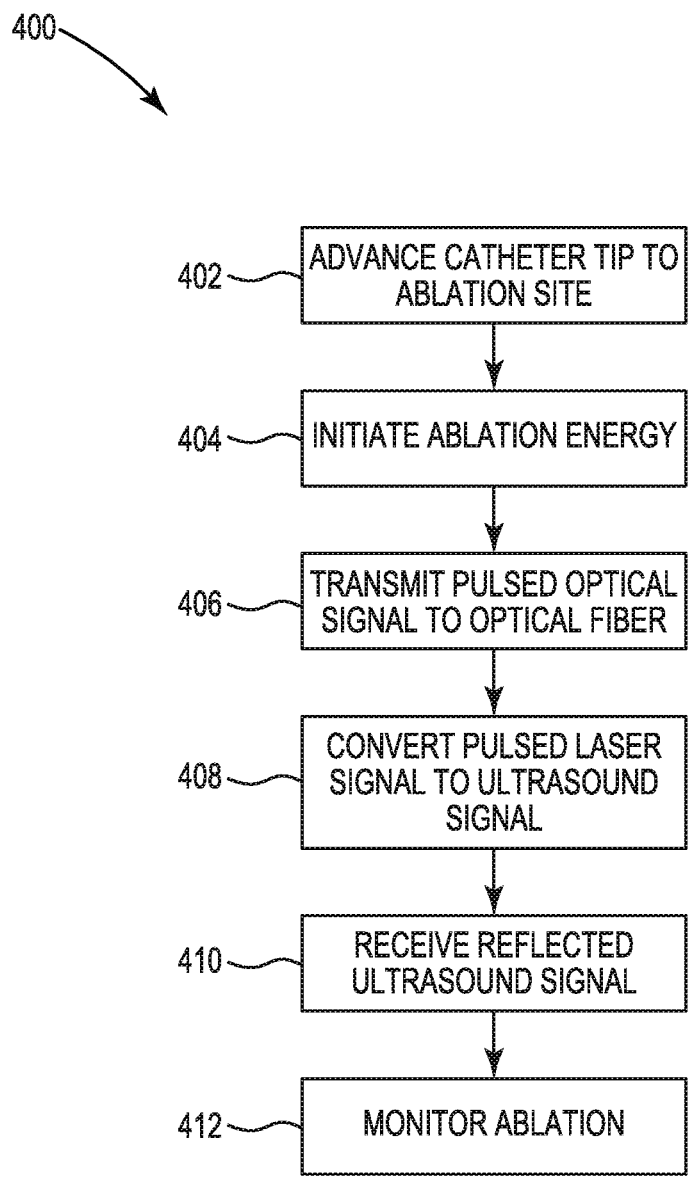
FIG. 4 outlines various steps of a routine, in accordance with certain embodiments of the present disclosure.

FIG. 3 shows the catheter tip 204 positioned adjacent to a target tissue ablation site 300 undergoing an ablation procedure. For clarity, the ablation electrode 206 is shown as not being in direct contact with the tissue—although, during ablation, the ablation electrode 206 typically is in direct contact with the tissue. FIG. 4 provides an example routine 400 that includes some of the functions or steps that can be carried out by various components of the system 100 (e.g., catheter 102/200, control system 150, optical source 164, and display 166) to assess, monitor, and control aspects of an ablation procedure.

During an ablation procedure, the catheter tip 204 is advanced near the target tissue ablation site 300 within a heart (step 402). In some embodiments, the catheter tip 204 is guided with assistance from the ultrasound assembly 210. For example, the optical-to-ultrasound transducing element 214 can generate and emit an ultrasound signal, which impinges upon tissue and gets reflected back to the ultrasound-to-optical transducing element 220. The reflected, converted optical signals can be used to generate images that can be used to assist in identifying the optimal and/or desired position of the catheter tip 204.

Once the catheter tip 204 is in position and in contact with the tissue ablation site 300, the energy source 162 can be initiated to provide radio-frequency energy to the ablation electrode 206 (step 404), which begins to ablate the tissue. In addition, the optical source 164 can be initiated to begin transmitting a pulsed laser to the emitting optical fiber 212 in the ultrasound assembly 210 (step 406). In response to the pulsed laser, the optical-to-ultrasound transducing element 214 generates and emits an ultrasound signal (e.g., ultrasound waves) that is directed (e.g., propagated) towards the tissue ablation site 300 (step 408).

During ablation, the structure of the tissue changes. Upon impinging on tissue, the ultrasound signal will be reflected differently with differing tissue structure (e.g., tissue damage, bubble generation). The different reflected ultrasound signal (e.g., ultrasound waves) can be converted to an optical signal by the ultrasound-to-optical transducing element 220 (step 410). The converted optical signal is communicated to the measurement sub-unit 156 of the control system 150 via the receiving optical fibers 218. The converted optical signal includes information (e.g., magnitude, phase, time-variation) that can be used to assess and monitor ablation in real-time (step 412).

At any given point in time during ablation, the structure of the tissue at target tissue ablation site 300 can differ at different depths of the tissue. For example, FIG. 3 shows tissue having three different areas (i.e., first stage 302, second stage 304, and third stage 306) each with different structural properties within the tissue. Each area represents portions of tissue at different stages of ablation, with the first area being the most damaged because of its proximity to the ablation electrode 206. These different stages will have different acoustic refraction characteristics and therefore will reflect an ultrasound signal differently.

As such, at any given point in time, the tissue will cause the reflected ultrasound signal (and therefore converted optical signal) to have a "signature" 308 indicative of the current structure(s) of the tissue along the tissue's depth and/or within an area or volume of the tissue. This signature 308 can be processed, analyzed, and displayed by the control system 150, for example, by using the measurement sub-unit 156, mapping sub-unit 158, display controller 160, and the display 166. The measurement sub-unit 156 is configured to receive the converted optical signal itself and/or signals that correspond to such signals (e.g., electrical signals results from an optical-to-electrical conversion).

The mapping sub-unit 158 and/or navigation sub-unit 161 receive mapping/positioning signals from various mapping, navigation sensors, and/or optical fibers coupled to the catheter 200 and determines physiological mapping and catheter position information. The display controller 160 outputs the results of the various sub-units to the display 166. For example, the display controller 160 can combine measurement, mapping, and positioning information—which can be gathered in real-time—and output such information to the display 166, which can display images generated by the various sub-units. In certain embodiments, the control system 150 is configured to generate, based on the reflected, converted ultrasound signals, A-scan or B-scan images of the being-ablated tissue which can be used to monitor changes in the tissue structure.

FIG. 3 shows an example single-dimension signature 308, which is represented pictorially by a plurality of pixels 310 overlying and extending along the depth of the tissue. Each pixel 310 can have different characteristics such as pixel contrast and pixel brightness. The combination of each pixel's various characteristics forms the signature 308.

During ablation, the tissue's signature at any given point will change, and that change and/or the rate of change can be assessed and monitored in real-time to determine various aspects of the ablation procedure (e.g., boiling, charring). In certain embodiments, signatures of the same section of tissue at different points in time are compared to determine whether the section of tissue has been ablated along its full depth or is only partially ablated. For example, certain pixels within a signature may have a higher brightness compared to the same pixels from previous signatures—and that difference in brightness can indicate that the tissue has become more damaged. In certain embodiments, signatures of different sections of tissue are compared to each other to determine whether portions of tissue have or have not been ablated or to identify the edge of the section of ablated tissue. For example, frequency of changes in brightness of a pixel or a group of pixels can indicate rapid changes in tissue properties. Tissue boiling, for example, would signal a higher frequency change in pixels and adjacent pixels indicating rapid or dynamic changes in tissue due to vaporization. Further, an interpixel brightness would change rapidly indicating rapid or dynamic changes in tissue.

In addition to assessing and monitoring tissue ablation, the control system 150 can use the converted optical signal (and resulting images) to control various aspects of the ablation procedure. In some embodiments, based on the converted optical signal and/or images, the control system 150 is configured to modify (1) the amount of and frequency of radio-frequency power provided by the energy source 162 to the ablation electrode 206, (2) the duration of radio-frequency energy is applied, (3) the flow rate of cooling fluid provided to the catheter tip 204, and/or (4) amount of pressure applied by the tip to the tissue. In some embodiments, the images can inform a technician or physician to move the catheter tip to another location or adjust the amount of pressure applied to the tissue.

The control system's memory 152 can include a computer-readable recording medium or other forms of memory for storing processor-executable instructions, data structures and other information. The memory 152 may comprise a non-volatile memory, such as read-only memory (ROM) and/or flash memory, and a random-access memory (RAM), such as dynamic random access memory (DRAM), or synchronous dynamic random access memory (SDRAM). In some embodiments, the memory 152 may store processor-executable instructions that, when executed by the processor 154, perform routines for carrying out the functions related to assessing, monitoring, and controlling various aspects of tissue ablation. It will be appreciated by those skilled in the art that computer-readable media can be any available media that may be accessed by the control system 150 or other computing systems and devices for the non-transitory storage of information. Computer-readable media includes volatile and non-volatile, removable and non-removable recording media implemented in any method or technology, including, but not limited to, RAM, ROM, erasable programmable ROM (EPROM), electrically-erasable programmable ROM (EEPROM), FLASH memory or other solid-state memory technology, compact disc ROM (CD-ROM), digital versatile disk (DVD), BLU-RAY or other optical storage, magnetic tape, magnetic disk storage or other magnetic storage devices and the like.

It will be also appreciated that the structure and/or functionality of the control system 150 may be different than that illustrated in FIG. 1 and described herein. For example, the processor 154, measurement sub-unit 156, mapping sub-unit 158, display controller 160, navigation sub-unit 161, and other components of the control system 150 may be integrated within a common integrated circuit package or distributed among multiple integrated circuit packages that together form control circuitry. It will be further appreciated that the control system 150 may not include all of the components shown in FIG. 1, may include other components that are not explicitly shown in FIG. 1 such as additional controllers dedicated to specific functions or steps in the routine 400 or described above, or may utilize an architecture different than that shown in FIG. 1.

Figure 5:
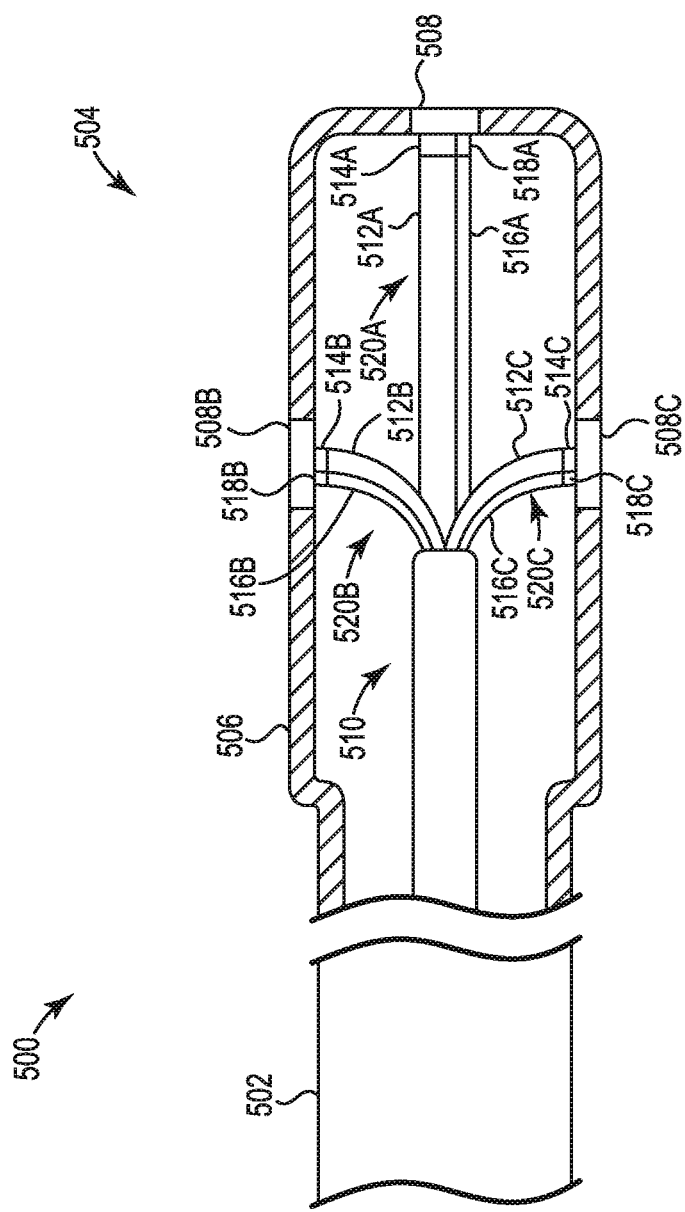
FIG. 5 shows a schematic side view of a portion of a catheter, in accordance with certain embodiments of the present disclosure.

FIG. 5 shows a cross-section view of a catheter 500, like catheter 102 of FIG. 1, that can be used in the system 100. The catheter 500 includes an elongated catheter body 502 and a catheter tip 504. The catheter 500 also includes an ablation electrode 506 coupled to the catheter tip 504. The catheter 500 is shown as including a plurality of windows 508A-C positioned centrally at and radially around the catheter tip 504.

The catheter 500 includes an ultrasound assembly 510 positioned within the catheter tip 504. The ultrasound assembly 510 consumes less volume within the catheter tip 504 compared to piezo-based ultrasound transducers. In some embodiments, the total diameter of the ultrasound assembly 510 at the catheter tip 504 can be 500 µm or less. It should be noted that the ultrasound assembly 510 and catheter tip 504 are not drawn to scale and that the catheter tip 504 can include features other than the ultrasound assembly 510, such as temperature sensors, navigation sensors, and fluid conduits, among other things. The ultrasound assembly 510, together with its various components, is configured to emit an ultrasonic signal and receive a responsive ultrasonic signal indicative of various tissue ablation parameters.

The ultrasound assembly 510 includes a plurality of optical fibers, including first, second, and third emitting optical fibers 512A, 512B, and 512C. Each emitting optical fiber 512A-C includes an optical-to-ultrasound transducing element 514A-C that is coupled to the emitting optical fiber at the distal end of the emitting optical fiber. Each emitting optical fiber 512A-C is also coupled to the optical source 164. The emitting optical fibers are configured to direct a pulsed or amplitude-modulated optical signal to the optical-to-ultrasound transducing elements, which are configured to generate and emit an ultrasound signal (e.g., ultrasound waves) that is directed (e.g., propagated) towards tissue undergoing ablation. The optical signal can be pulsed at ultrasonic frequencies. In some embodiments, the optical-to-ultrasound transducing element 514A-C is a coating at the distal end that is configured to rapidly expand and contract to generate an ultrasound signal. The coating expands and contracts in response to a quickly-pulsing optical signal that is communicated to the coating via the emitting optical fibers. The pulsed optical signal rapidly heats and cools the coating such that the coating rapidly expands and contracts.

The coating can comprise elastomers (e.g., polydimethylsiloxane), carbon nanotubes, gold nanostructures, polymers, graphene, carbon black, graphite, and various combinations of such materials. In some implementations, the coating is applied to the distal end of the emitting optical fibers, and in other embodiments, an intervening material is positioned between the coating and the distal end of the emitting optical fibers.

The ultrasound assembly 510 also includes first, second, and third receiving optical fibers 516A-C coupled to corresponding ultrasound-to-optical transducing elements 518A-C. The ultrasound-to-optical transducing elements 518A-C are configured to convert an ultrasound signal (including its magnitude, phase, and time-variation) reflected from tissue to a corresponding optical signal. For example, each ultrasound-to-optical transducing element 518A-C is configured to change its optical properties upon being excited by an ultrasound signal (e.g., ultrasound waves). In some embodiments, the ultrasound-to-optical transducing elements are interferometers (e.g., a Fabry-Perot cavity) mounted at a distal end of the receiving optical fibers. In other embodiments, the ultrasound-to-optical transducing elements are micro-ring optical resonators. The resulting optical signal is communicated via the receiving optical fibers to the control system 150 for analysis, processing, etc.

As shown in FIG. 5, the ultrasound assembly 510 includes multiple pairs of emitting and receiving optical fibers. The first pair 520A includes emitting and receiving optical fibers 512A and 516A; the second pair 520B includes emitting and receiving optical fibers 512B and 516B; and the third pair 520C includes emitting and receiving optical fibers 512C and 516C. Each pair is directed in a different direction than the other pairs. For example, the first pair 520A is aligned with the window 508A positioned centrally at a distal end of the catheter tip 504. The second pair 520B is aligned with the window 508B positioned radially around the catheter tip 504. And the third pair 520C is aligned with the window 508C positioned radially around the catheter tip 504. Although only three pairs of emitting and receiving optical fibers are shown in FIG. 5, the ultrasound assembly 510 could have additional or fewer pairs of optical fibers, for example, three or four pairs aligned with windows positioned radially around the catheter tip 504.

Figure 6:
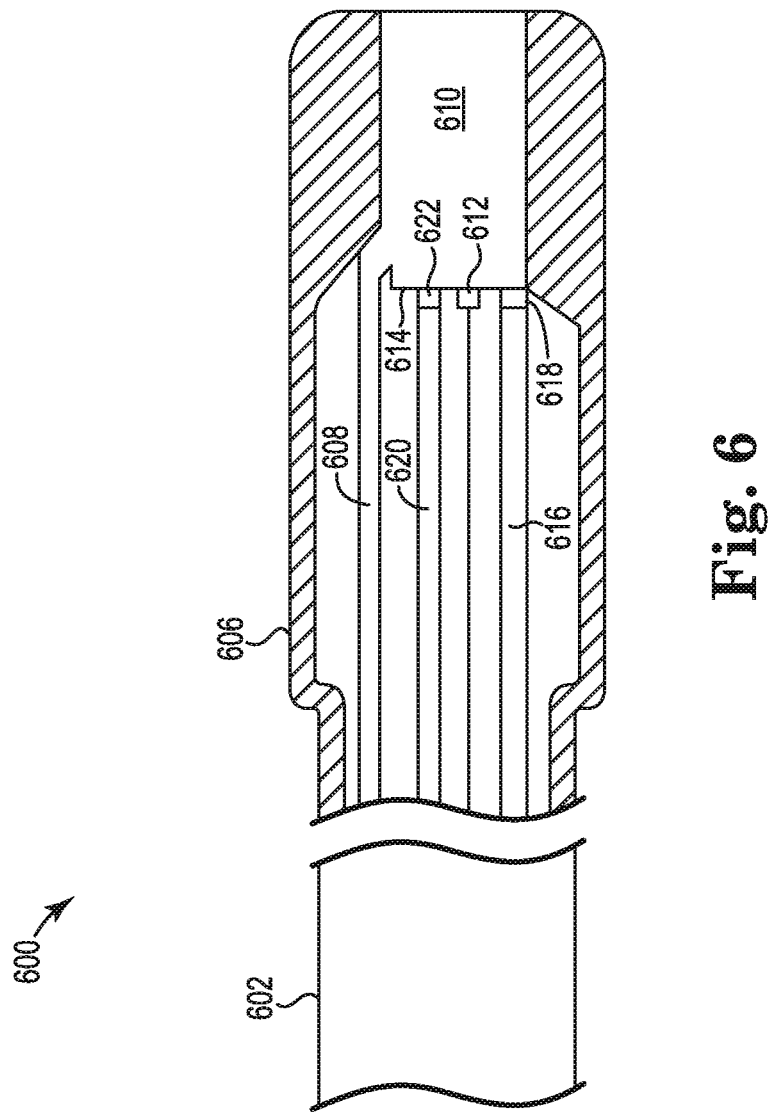
FIG. 6 shows a schematic side view of a portion of a catheter, in accordance with certain embodiments of the present disclosure.

FIG. 6 shows a cross-section view of a catheter 600, like catheter 102 of FIG. 1, that can be used in the system 100. The catheter 600 includes an elongated catheter body 602 and a catheter tip 604. The catheter 600 also includes an ablation electrode 606 coupled to the catheter tip 604. The catheter 600 further includes a fluid conduit 608 through which cooling fluid can flow. The fluid conduit 608 is coupled to a cooling chamber 610 in the catheter tip 604. The cooling fluid is used during ablation to control the temperature of the ablation electrode 608 and/or tissue. For example, the cooling fluid can keep the being-ablated tissue from charring. The catheter 600 also includes a temperature sensor 612 (e.g., thermocouple) positioned at a proximal end 614 of the cooling chamber 610. It should be noted that the catheter tip 604 and its features are not drawn to scale and that the catheter tip 604 can include other features such as navigation sensors, among other things.

The catheter 600 includes a plurality of optical fibers, including an emitting optical fiber 616. The emitting optical fiber 616 includes an optical-to-ultrasound transducing element 618 that is coupled to the emitting optical fiber 616 at a distal end of the emitting optical fiber 616. The emitting optical fiber 616 is also coupled to the optical source 164. The emitting optical fiber 616 is configured to direct a pulsed or amplitude-modulated optical signal to the optical-to-ultrasound transducing element 618, which is configured to generate and emit an ultrasound signal (e.g., ultrasound waves) that is directed (e.g., propagated) towards tissue undergoing ablation. The optical signal can be pulsed at ultrasonic frequencies. In some embodiments, the optical-to-ultrasound transducing element 618 is a coating at the distal end that is configured to rapidly expand and contract to generate an ultrasound signal. The coating expands and contracts in response to a quickly-pulsing optical signal that is communicated to the coating via the emitting optical fiber 616. The pulsed optical signal rapidly heats and cools the coating such that the coating rapidly expands and contracts.

The coating can comprise elastomers (e.g., polydimethylsiloxane), carbon nanotubes, gold nanostructures, polymers, graphene, carbon black, graphite, and various combinations of such materials. In some implementations, the coating is applied to the distal end of the emitting optical fiber 616, and in other embodiments, an intervening material is positioned between the coating and the distal end of the emitting optical fiber 616.

The catheter 600 also includes a receiving optical fiber 620 coupled to ultrasound-to-optical transducing element 622. The ultrasound-to-optical transducing element 622 is configured to convert an ultrasound signal (including its magnitude, phase, and time-variation) reflected from tissue to a corresponding optical signal. For example, the ultrasound-to-optical transducing element 622 is configured to change its optical properties upon being excited by an ultrasound signal (e.g., ultrasound waves). In some embodiments, the ultrasound-to-optical transducing element 622 is an interferometer (e.g., a Fabry-Perot cavity) that is mounted at a distal end of the receiving optical fiber 620. In other embodiments, the ultrasound-to-optical transducing element 622 is a micro-ring optical resonator. The resulting optical signal is communicated via the receiving optical fiber 620 to the control system 150 for analysis, processing, etc.

The optical fibers extend along the catheter 600 such that the emitting optical fiber 616 is coupled to the laser source 164 and the receiving optical fiber 620 is coupled to the measurement sub-unit 156 of the control system 150. The optical fibers extend through the catheter tip 604 to the proximal end 614 of the cooling chamber 610. During ablation, the cooling fluid can help control the temperature of the optical fibers at their tip. The temperature sensor 612 can monitor the temperature of the tips of the optical fibers. In certain embodiments, the measured temperature can be used to determine whether more or less cooling fluid should be directed to the cooling chamber 610 to maintain or change temperature of the tips of the optical fibers.

The proximal end 614 of the cooling chamber 610 may include a window or otherwise comprise an ultrasound-transparent material such that, upon receiving a pulsed optical signal from the emitting optical fiber 616, the optical-to-ultrasound transducing element 618 can generate and emit an ultrasound signal directed towards tissue undergoing ablation. The ultrasound signal impinges upon the tissue and is, at least partially, reflected back towards the ultrasound-to-optical transducing elements 622, which converts the reflected ultrasound signal to an optical signal that is communicated via the receiving optical fibers 620 to the control system 150. The control system 150, together with its various components, is configured to receive the converted optical signal and use the converted optical signal to assess, monitor, and control various aspects of an ablation procedure in real-time.

The emitting optical fiber 616 has a larger diameter than the receiving optical fiber 620 because the emitting optical fiber 616 is configured to communicate a greater amount of optical energy to cause the optical-to-ultrasound transducing element 618 to rapidly heat and cool. The receiving optical fiber 620 can be a single-mode optical fiber, which can have a diameter that are less than a fifth of the diameter of the emitting optical fiber 616. The catheter 600 can feature additional emitting fibers (each with an optical-to-ultrasound transducing element) and/or fewer or more receiving optical fibers (each with an ultrasound-to-optical transducing element).

Figure 7:
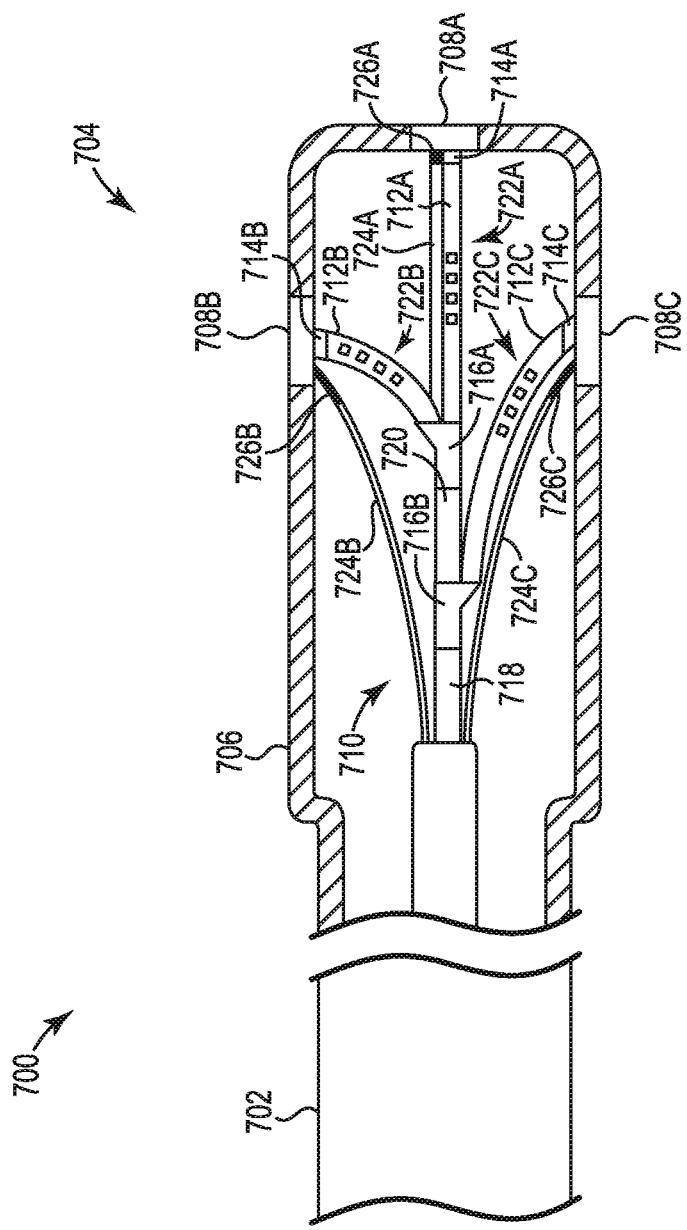
FIG. 7 shows a schematic side view of a portion of a catheter, in accordance with certain embodiments of the present disclosure.

FIG. 7 shows a cross-section view of a catheter 700, like catheter 102 of FIG. 1, that can be used in the system 100. The catheter 700 includes an elongated catheter body 702 and a catheter tip 704. The catheter 700 also includes an ablation electrode 706 coupled to the catheter tip 704. The catheter 700 is shown as including a plurality of windows 708A-C positioned centrally at and radially around the catheter tip 704.

The catheter 700 includes an ultrasound assembly 710 positioned within the catheter tip 704. The ultrasound assembly 710 consumes less volume within the catheter tip 704 compared to piezo-based ultrasound transducers. In some embodiments, the total diameter of the ultrasound assembly 710 at the catheter tip 704 can be 500 μm or less. It should be noted that the ultrasound assembly 710 and catheter tip 704 are not drawn to scale and that the catheter tip 704 can include features other than the ultrasound assembly 710, such as temperature sensors, navigation sensors, and fluid conduits, among other things. The ultrasound assembly 710, together with its various components, is configured to emit an ultrasonic signal and receive a responsive ultrasonic signal indicative of various tissue ablation parameters.

The ultrasound assembly 710 includes a plurality of optical fibers, including first, second, and third emitting optical fibers 712A, 712B, and 712C. Each emitting optical fiber 712A-C includes an optical-to-ultrasound transducing element 714A-C that is coupled to the emitting optical fiber at the distal end of the emitting optical fiber. Each emitting optical fiber 712A-C is also coupled to the optical source 164, which can include a plurality of sources. For example, the optical source 164 can include multiple lasers that are each configured to generate light at different wavelengths.

The emitting optical fibers are configured to direct a pulsed or amplitude-modulated optical signal to the optical-to-ultrasound transducing elements, which are configured to generate and emit an ultrasound signal (e.g., ultrasound waves) that is directed (e.g., propagated) towards tissue undergoing ablation. As will be described in more detail below, each optical-to-ultrasound transducing element is configured to generate an ultrasonic signal at a frequency that is different than the other optical-to-ultrasound transducing elements. For example, the optical signal directed towards each optical-to-ultrasound transducing element is pulsed at a different frequency than the optical signals directed towards the other optical-to-ultrasound transducing elements. In some embodiments, the optical-to-ultrasound transducing element 714A-C is a coating at the distal end that is configured to rapidly expand and contract to generate an ultrasound signal. The coating expands and contracts in response to a quickly-pulsing optical signal that is communicated to the coating via the emitting optical fibers. The pulsed optical signal rapidly heats and cools the coating such that the coating rapidly expands and contracts.

The coating can comprise elastomers (e.g., polydimethylsiloxane), carbon nanotubes, gold nanostructures, polymers, graphene, carbon black, graphite, and various combinations of such materials. In some implementations, the coating is applied to the distal end of the emitting optical fibers, and in other embodiments, an intervening material is positioned between the coating and the distal end of the emitting optical fibers.

The ultrasound assembly 710 also includes first and second optical couplers, 716A and 716B. Each of the first and second optical couplers, 716A and 716B, splits light into separate optical fibers. For example, the second optical coupler 716B is shown in FIG. 7 as splitting light from a single optical fiber 718 to an intermediate optical fiber 720 and the third emitting optical fiber 712C. The first optical coupler 716A splits light from the intermediate optical 720 to the first and second emitting optical fibers, 712A and 712B. Each of the emitting optical fibers includes a Fiber-Bragg grating 722A, 722B, and 722C. Each Fiber-Bragg grating is configured to reflect (e.g., filter) predetermined wavelengths such that certain wavelengths pass through the grating. In embodiments, each Fiber-Bragg grating is configured to reflect wavelengths different than the other Fiber-Bragg gratings. As a result, a different wavelength or wavelengths of light, which can be generated from the plurality of optical sources, are directed to each optical-to-ultrasound transducing element 714A-C. Each wavelength or set of wavelengths can be pulsed at different frequencies such that the optical-to-ultrasound transducing elements 714A-C generate ultrasonic signals at different wavelengths.

The ultrasound assembly 710 also includes first, second, and third receiving optical fibers 724A-C coupled to corresponding ultrasound-to-optical transducing elements 726A-C. The ultrasound-to-optical transducing elements 726A-C are configured to convert an ultrasound signal (including its magnitude, phase, and time-variation) reflected from tissue to a corresponding optical signal. For example, each ultrasound-to-optical transducing element 726A-C is configured to change its optical properties upon being excited by an ultrasound signal (e.g., ultrasound waves). In some embodiments, the ultrasound-to-optical transducing elements are interferometers (e.g., a Fabry-Perot cavity) mounted at a distal end of the receiving optical fibers. In other embodiments, the ultrasound-to-optical transducing elements are micro-ring optical resonators. The resulting optical signals are communicated via the receiving optical fibers to the control system 150 for analysis, processing, etc. The resulting optical signals can be optically multiplexed for further analysis, processing, etc.

As shown in FIG. 7, the ultrasound assembly 710 includes multiple pairs of emitting and receiving optical fibers. The first pair includes emitting and receiving optical fibers 712A and 724A; the second pair includes emitting and receiving optical fibers 712B and 724B; and the third pair includes emitting and receiving optical fibers 712C and 724C. Each pair is directed in a different direction than the other pairs. For example, the first pair is aligned with the window 708A positioned centrally at a distal end of the catheter tip 704. The second pair is aligned with the window 708B positioned radially around the catheter tip 704. And the third pair is aligned with the window 708C positioned radially around the catheter tip 704. Although only three pairs of emitting and receiving optical fibers are shown in FIG. 7, the ultrasound assembly 710 could have additional or fewer pairs of optical fibers, for example, three or four pairs aligned with windows positioned radially around the catheter tip 704.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:
1. A catheter system comprising:
 a catheter comprising:
  a catheter tip,
  a plurality of windows proximate to the catheter tip, and
  an ultrasound assembly at least partially positioned within the catheter tip, the ultrasound assembly comprising:
   a first optical fiber coupled to a first optical-to-ultrasound transducer, the first optical-to-ultrasound transducer configured to generate an ultrasound signal in response to a pulsed optical signal, and
   a second optical fiber coupled to a first ultrasound-to-optical transducer, the first ultrasound-to-optical transducer configured to generate an optical signal in response to a received ultrasound signal,
   a third optical fiber coupled to a second optical-to-ultrasound transducer, the second optical-to-ultrasound transducer configured to generate an ultrasound signal in response to a pulsed optical signal, and
   a fourth optical fiber coupled to a second ultrasound-to-optical transducer, the second ultrasound-to-optical transducer configured to generate an optical signal in response to a received ultrasound signal,
   wherein the first optical fiber and the second optical fiber are aligned with a first window of the plurality of windows,
   wherein the third optical fiber and the fourth optical fiber are aligned with a second window of the plurality of windows.

2. The catheter system of claim 1, wherein the first optical-to-ultrasound transducer is a coating applied to a distal end of the first optical fiber.

3. The catheter system of claim 2, wherein the coating comprises at least one of an elastomer, carbon nanotubes, gold nanostructures, polymer, carbon black, graphene, and graphite.

4. The catheter system of claim 1, wherein the ultrasound assembly further comprises:
 a sixth optical fiber coupled to a third ultrasound-to-optical transducer, the third ultrasound-to-optical transducer configured to generate an optical signal in response to a received ultrasound signal.

5. The catheter system of claim 4, wherein the first optical fiber is positioned centrally among the other optical fibers.

6. The catheter system of claim 1, wherein the first optical fiber has a greater diameter than the other optical fibers.

7. The catheter system of claim 1, wherein the catheter tip includes a cooling chamber, and wherein a distal end of the first optical fiber is coupled to a proximal end of the cooling chamber.

8. The catheter system of claim 7, further comprising:
a temperature sensor positioned within the catheter tip adjacent the distal end of the first optical fiber.

9. The catheter system of claim 1, wherein the optical signal corresponds to a signature of a tissue structure.

10. The catheter system of claim 9, further comprising:
a control system comprising a memory and a processor, wherein the memory stores instructions that cause the processor to:
receive the optical signal,
compare the signature to a previously-received signature, and
based on the comparison, determine that the tissue has been ablated.

11. The catheter system of claim 10, wherein the signature comprises a plurality of pixels, each of which is indicative of tissue structure at different depths of the tissue, and wherein the comparison includes comparing one of pixel brightness and pixel contrast.

12. The catheter system of claim 9, further comprising:
a control system comprising a memory and a processor, wherein the memory stores instructions that cause the processor to:
receive the optical signal,
compare a signature of a first portion of tissue to a signature of a second portion of tissue, and
based on the comparison, determine that the first portion of tissue has been ablated.

13. The catheter system of claim 12, wherein the signature comprises a plurality of pixels, each of which is indicative of tissue structure at different depths of the tissue, and wherein the comparison includes comparing one of pixel brightness and pixel contrast.

14. The catheter system of claim 1, wherein the first optical fiber includes a first set of optical gratings, wherein the first optical-to-ultrasound transducer is configured to generate an ultrasound signal at a first frequency, wherein the third optical fiber includes a second set of optical gratings, wherein the second optical-to-ultrasound transducer is configured to generate an ultrasound signal at a second frequency, and wherein the catheter further comprises:
a fifth optical fiber coupled to a third optical-to-ultrasound transducer and having a third set of optical gratings, wherein the third optical-to-ultrasound transducer is configured to generate an ultrasound signal at a third frequency.

15. The catheter system of claim 14, further comprising:
a first optical coupler configured to split light between an intermediate optical fiber and the fifth optical fiber; and
a second optical coupler configured to split light from the intermediate optical fiber to the third and first optical fibers.

* * * * *